United States Patent [19]

Williams

[11] Patent Number: Plant 6,673

[45] Date of Patent: Mar. 14, 1989

[54] MINIATURE ROSE PLANT/MINADCO

[76] Inventor: Ernest D. Williams, 1510 Lebanon Ave., Dallas, Tex. 75208

[21] Appl. No.: 43,815

[22] Filed: Apr. 29, 1987

[51] Int. Cl.[4] ..... A01H 5/00

[52] U.S. Cl. ..... Plt./7

[58] Field of Search ..... Plt./7

*Primary Examiner*—Robert E. Bagwill

[57] ABSTRACT

This invention relates to a new and distinct variety of miniature rose plant primarily identified by the unusual mauve color, the petals being purple on outside surface and a similar purple on inside surface.

1 Drawing Sheet

The present invention relates to a new and distinct variety of hardy, dwarf, bush type rose plant of the miniature class; the variety being primarily characterized — as to novelty — by the purple of the outside surface of petals and the similar purple of inside surface and the Hybrid Tea form of buds and flowers.

The variety is further characterized by:

An abundance of bloom, with flowers usually borne, singly, but also several to the stem in loose clusters.

Heavy fragrance.

A plant which is vigorous, of rounded, upright shape with small semi-glossy to matt foliage with pointed leaflets; the buds and flowers being similar in form and size to Over the Rainbow (miniature — U.S. Plant Pat. No. 3,472).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Mini-Roses Nursery located at Dallas, Tex., under conditions of careful control and observation, as a cross between Angelface (U.S. Plant Pat. No. 2,792 expired — Florabunda) as the seed parent and Anita Charles (miniature — U.S. Plant Pat. No. 5,110) as the pollen parent.

Subsequent to origination of the variety I successfully asexually reproduced it at Mini-Roses Nursery, located as aforesaid, by cuttings; the reproductions having run true in all respects.

The color photograph illustrates the variety, including the foliage, buds, and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Type: Hardy; dwarf; bushy; upright; seedling; greenhouse; outdoors; cut flowers; garden decoration; potted plant.

Class: miniature. Variety identification: Minadco. (Commercial synonym: Royalglo).

Flowers borne: Singly and several together (3 to 5) on slender wirey stems.

Quantity of bloom: Abundant both outside and in greenhouse.

Bud:

*Peduncle.*—Medium to long; slender but sturdy; erect; medium green, sometimes tinted bronze (outdoors); with no prickles and few or no short hairs.

*Before calyx breaks; size.*—Small. Form long; pointed with several foliaceous apendages on surface of bud; with foliaceous parts extending beyond the tip of the bud equal to one-half or less of its length.

*Color.*—Medium to dark green, occasionally tinted with bronze (outdoors).

*As calyx breaks, color.*—Mauve.

*Opening.*—Opens well in all weather.

Bloom:

*Size when fully open.*—Small, averaging about 35 mm (1½").

*Petalage.*—Double — averaging about 40 petals arranged reguarly plus several small petaloids.

*Form.*—High centered with petals rolled loosely outward and downward. Open flowers usually show stamens.

Petals: Fairly thick; satiny on inside and on outside surface.

*Shape.*—Outside petals, broad lanceolate (nearly round), without acute tip; intermediate — broad lanceolate without acute tip, inside — lanceolate without acute tip.

Color: Newly opened flower from a plant grown outside (July 1985), Dallas, Tex.

*Outside petal.*—Outside surface — a coloring similar to Greyed — purple 186 (A and B) but varying some, both lighter and darker, depending upon factors such as light intensity and growing conditions, with a small near white area at base. Inside surface — similar to outside surface but may be slightly lighter in color. The satiny petal surface reflects some of the light thus giving the petal surface the apprearance of being lighter in color.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — mauve (purple). Three days open — color mauve (purple). Behavior — opens well in all weather. Spent petals drop off.

Flower longevity (July 1985) — plant in pot 4–5 days or longer. Cut flowers at living room temperature 4–5 days or longer.

Reproductive organs:

*Stamens.*—Fair amount.

*Filaments.*—Fair amount, varying length, medium long.

*Anthers.*—Yellow.

*Pollen.*—Some.

*Pistils.*—Average number.

*Styles.*—Varying length; purple; short and regular.

*Ovaries.*—All enclosed in calyx.

*Hips.*—Few.

*Sepals.*—Permanent; spear shaped; recurved.

*Seed.*—Few, 3–5.

Foliage:

*Leaves.*—Compound of five (sometimes three to seven) leaflets; medium small; leathery; semi-glossy to matt.

*Leaflets.*—Shape: broad, nearly oval; apex acute; base rounded — sometimes acute.

*Color.*—Medium green; new growth — normal (medium) green (sometimes tinted reddish).

*Rachis.*—Medium strength; upper side may have several tiny short hairs; grooved; underside may have several thorns (1–3).

*Stipules.*—medium to short length; medium width; medium length narrow points which turn out usually at about 45 degrees or more.

Growth:

*Habit.*—Dwarf; bushy; upright; much branched.

*Growth.*—Free; vigorous; internodes short.

*Canes.*—Medium; slender; sturdy.

*Main stems.*—Color: medium green.

*Thorns.*—Average declining dialated at base. Prickles — none. Hairs — none.

*Branches.*—Color: medium green. Thorns: average; slender; prickles: none. Hairs — none The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flower of exhibition form, essentially mauve in color, the petals on outside surface being same as on inside surface, and further characterized by a plant of compact well rounded shape; vigorous, with the main stems and shoots being of average thorniness, the said plant being easy to propagate from cuttings or by budding, with an abundance of flowers borne singly or several to the stem in loose clusters.

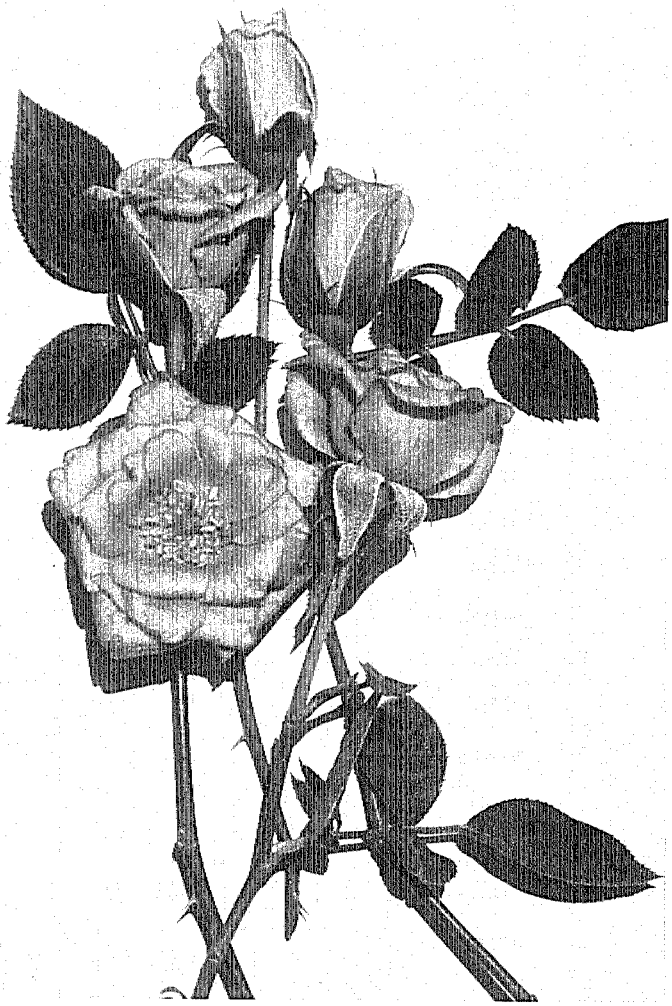

* * * * *